US00PP15916P2

(12) United States Plant Patent
Blay et al.

(10) Patent No.: US PP15,916 P2
(45) Date of Patent: Aug. 9, 2005

(54) ***LILIUM* PLANT NAMED 'MISS LUCY'**

(50) Latin Name: *Lilium hybrida*
Varietal Denomination: Miss Lucy

(75) Inventors: John William Blay, Kaiapoi (NZ); Violet Marilyn Blay, Kaiapoi (NZ)

(73) Assignee: License Institute Netherlands, Steenbergen (NL)

( * ) Notice: Subject to any disclaimer, the term of this patent is extended or adjusted under 35 U.S.C. 154(b) by 70 days.

(21) Appl. No.: 10/888,832

(22) Filed: Jul. 9, 2004

(51) Int. Cl.[7] ..... A01H 5/00

(52) U.S. Cl. ..... Plt./315

(58) Field of Search ..... Plt./315

(56) References Cited

U.S. PATENT DOCUMENTS

PP8,313 P * 7/1993 Vletter ..... Plt./315
PP8,322 P * 7/1993 Vletter ..... Plt./315
PP9,614 P * 7/1996 Van Der Voort ..... Plt./315

OTHER PUBLICATIONS

UPOV ROM GTITM Computer Database, GTI Jouve Retrieval Software 2004/40 Citation for 'Miss Lucy'.*
http://www.mailordergardening.com/MGA_GTA_2004_Winners.pdf.*

* cited by examiner

*Primary Examiner*—Kent Bell
*Assistant Examiner*—W. C. Haas
(74) *Attorney, Agent, or Firm*—C. A. Whealy

(57) ABSTRACT

A new and distinct cultivar of *Lilium* plant named 'Miss Lucy', characterized by its erect and strong flowering stems; vigorous growth habit; double flowers; white and pink-colored flowers; and good postproduction longevity.

2 Drawing Sheets

Botanical designation: *Lilium hybrida.*
Variety denomination: 'Miss Lucy'.

BACKGROUND OF THE INVENTION

The present Invention relates to a new and distinct cultivar of *Lilium* plant, botanically known as *Lilium hybrida,* commercially used as a cut flower Oriental *Lilium,* and hereinafter referred to by the name 'Miss Lucy'.

The new *Lilium* is a product of a planned breeding program conducted by the Inventors in Kaiapoi, New Zealand. The objective of the breeding program was to develop new cut flower *Lilium* cultivars with double flowers.

The new *Lilium* originated from a cross-pollination made by the Inventors in Kaiapoi, New Zealand, of two unnamed selections of *Lilium hybrida,* not patented. The new *Lilium* was discovered and selected by the Inventors as a single flowering plant within the progeny of the stated cross-pollination in a controlled environment in Kaiapoi, New Zealand.

Asexual reproduction of the new cultivar by bulb scaling in a controlled environment in Kaiapoi, New Zealand, since 1996, has shown that the unique features of this new *Lilium* are stable and reproduced true to type in successive generations of asexual propagation.

SUMMARY OF THE INVENTION

Plants of the cultivar Miss Lucy have not been observed under all possible environmental conditions. The phenotype may vary somewhat with variations in environment such as temperature and light intensity without, however, any variance in genotype.

The following traits have been repeatedly observed and are determined to be the unique characteristics of 'Miss Lucy'. These characteristics in combination distinguish 'Miss Lucy' as a new and distinct cultivar:

1. Erect and strong flowering stems.
2. Vigorous growth habit.
3. Double flowers.
4. White and pink-colored flowers.
5. Good postproduction longevity.

Plants of the new *Lilium* can be compared to plants of the cultivar Marco Polo, disclosed in U.S. Plant Pat. No. 8,322. In side-by-side comparisons conducted in Kaiapoi, New Zealand, plants of the new *Lilium* differed from plants of the cultivar Marco Polo in the following characteristics:

1. Plants of the new *Lilium* had double flowers whereas plants of the cultivar Marco Polo had single flowers.
2. Flowers of plants of the new *Lilium* did not develop reproductive structures whereas flowers of plants of the cultivar Marco Polo developed reproductive structures.

Plants of the new *Lilium* can also be compared to plants of the cultivar Acapulco, disclosed in U.S. Plant Pat. No. 8,313. In side-by-side comparisons conducted in Kaiapoi, New Zealand, plants of the new *Lilium* differed from plants of the cultivar Acapulco in the following characteristics:

1. Plants of the new *Lilium* flowered later than plants of the cultivar Acapulco.
2. Plants of the new *Lilium* had double flowers whereas plants of the cultivar Acapulco had single flowers.
3. Flowers of plants of the new *Lilium* did not develop reproductive structures whereas flowers of plants of the cultivar Acapulco developed reproductive structures.
4. Plants of the new *Lilium* and the cultivar Acapulco differed in flower color.

BRIEF DESCRIPTION OF THE PHOTOGRAPHS

The accompanying colored photographs illustrate the overall appearance of the new *Lilium,* showing the colors as true as it is reasonably possible to obtain in colored reproductions of this type. Colors in the photographs may differ slightly from the color values cited in the detailed botanical description which accurately describe the colors of the new *Lilium*.

The photograph on the first sheet comprises a side perspective view of a typical flowering stem of 'Miss Lucy' without flowers.

The photograph on the second sheet comprises a close-up view of typical flowers of 'Miss Lucy'.

DETAILED BOTANICAL DESCRIPTION

The aforementioned photographs and following observations and measurements describe plants of the new *Lilium* grown in Kaiapoi, New Zealand in a glass-covered greenhouse in ground beds. During the production of the plants, day temperatures ranged from 2 to 22° C., night temperatures ranged from −3 to 18° C. and light levels averaged 15,000 lux. Plants used for the photographs and description were about six months old. The photographs and the description were taken during January and February. Color references are made to The Royal Horticultural Society Colour Chart, 1995 Edition, except where general terms of ordinary dictionary significance are used.

Botanical classification: *Lilium hybrida* cultivar Miss Lucy.

Parentage: Cross-pollination of two unnamed selections of *Lilium hybrida*, not patented.

Propagation:

*Type.*—By bulb scaling.

*Root description.*—Fibrous, fleshy, thick; close to 155D, in color.

*Rooting habit.*—Freely branching.

Plant description:

*Plant habit.*—Upright and erect flowering stems. Vigorous growth habit.

*Time from planting to harvest of cut flowers.*—About six months.

*Number of flowering stems produced per season.*—One.

*Plant height.*—About 120 cm.

*Plant diameter* (*spread*).—About 30 to 40 cm .

*Flowering stem description.*—Aspect: Erect. Length: About 120 cm. Diameter: About 7 cm. Strength: Strong. Texture: Glabrous. Color: Close to 137B.

*Foliage description.*—Arrangement: Alternate; simple. Quantity: About 45 to 60 per flowering stem. Length: About 12 to 15 cm. Width: About 3 to 4 cm. Shape: Lanceolate. Apex: Acute. Base: Attenuate. Margin: Entire. Texture, upper and lower surfaces: Smooth, glabrous; leathery. Venation pattern: Parallel. Petiole length: About 8 mm. Petiole diameter: About 3 to 4 mm. Petiole texture, upper and lower surfaces: Smooth. Color: Developing foliage, upper and lower surfaces: 137B. Fully expanded foliage, upper and lower surfaces: 137A. Venation, upper surface: 158A. Venation, lower surface: 138C. Petiole: 139D.

Flower description:

*Flower type and habit.*—Double flowers arranged in terminal racemes. Perianth segments separate. Flowers face outwardly. Flowers not persistent.

*Natural flowering season.*—Flowering continuous during the summer in New Zealand.

*Fragrance.*—Sweet.

*Flower longevity on the plant.*—About two to three weeks.

*Flower longevity as a cut flower.*—About 1.5 to 2.5 weeks.

*Flower buds.*—Length: About 8 to 10 cm. Diameter: About 3 to 4 cm. Shape: Lanceolate. Color: 155C overlain with 144A.

*Flower diameter.*—About 12 to 15 cm.

*Perianth.*—Arrangement: About 18 to 24 segments arranged in several whorls. Segment length: About 8 to 10 cm. Segment width: About 1.5 to 2.5 cm. Segment shape: Lanceolate. Segment apex: Acute. Segment base: Attenuate. Segment margin: Entire; undulate. Segment texture, upper and lower surfaces: Smooth, glabrous; velvety. Segment color: When opening and fully opened, upper surface: 155C; towards the apex, 73B; venation, 62A. When opening and fully opened, lower surface: 155C; venation, 142D.

*Peduncles.*—Length: About 10 to 15 cm. Diameter: About 5 mm. Strength: Strong. Angle: About 20 to 30° from vertical. Texture: Smooth, glabrous. Color: 137B.

*Reproductive organs.*—Development of reproductive organs has not been observed.

*Seed/fruit.*—Seed and fruit development has not been observed.

Disease/pest resistance: Plants of the new *Lilium* have not been observed to be resistant to pathogens and pests common to *Lilium*.

Temperature tolerance: Plants of the new *Lilium* have been observed to tolerate temperatures from 0 to 38° C.

It is claimed:

1. A new and distinct cultivar of *Lilium* plant named 'Miss Lucy', as illustrated and described.

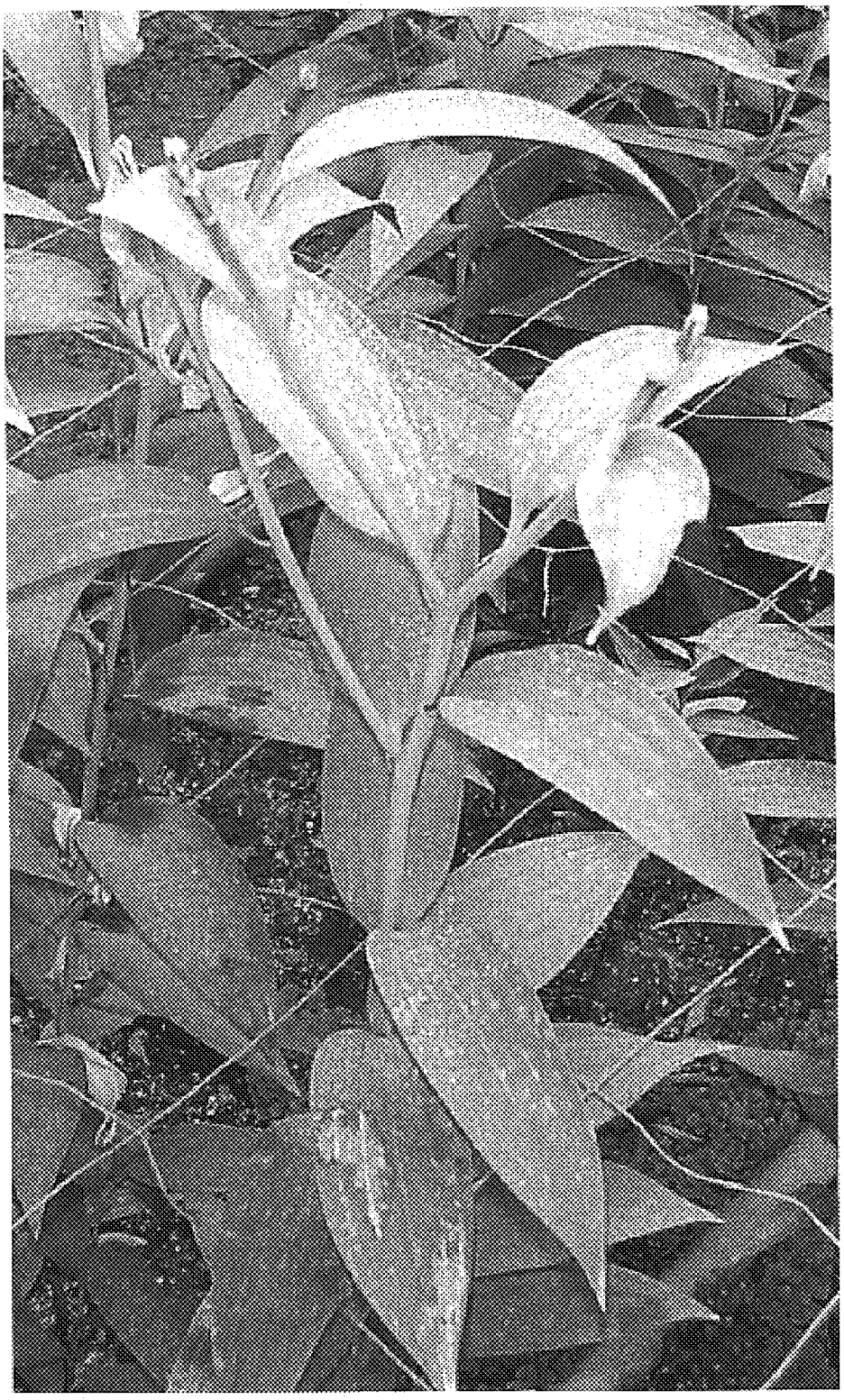

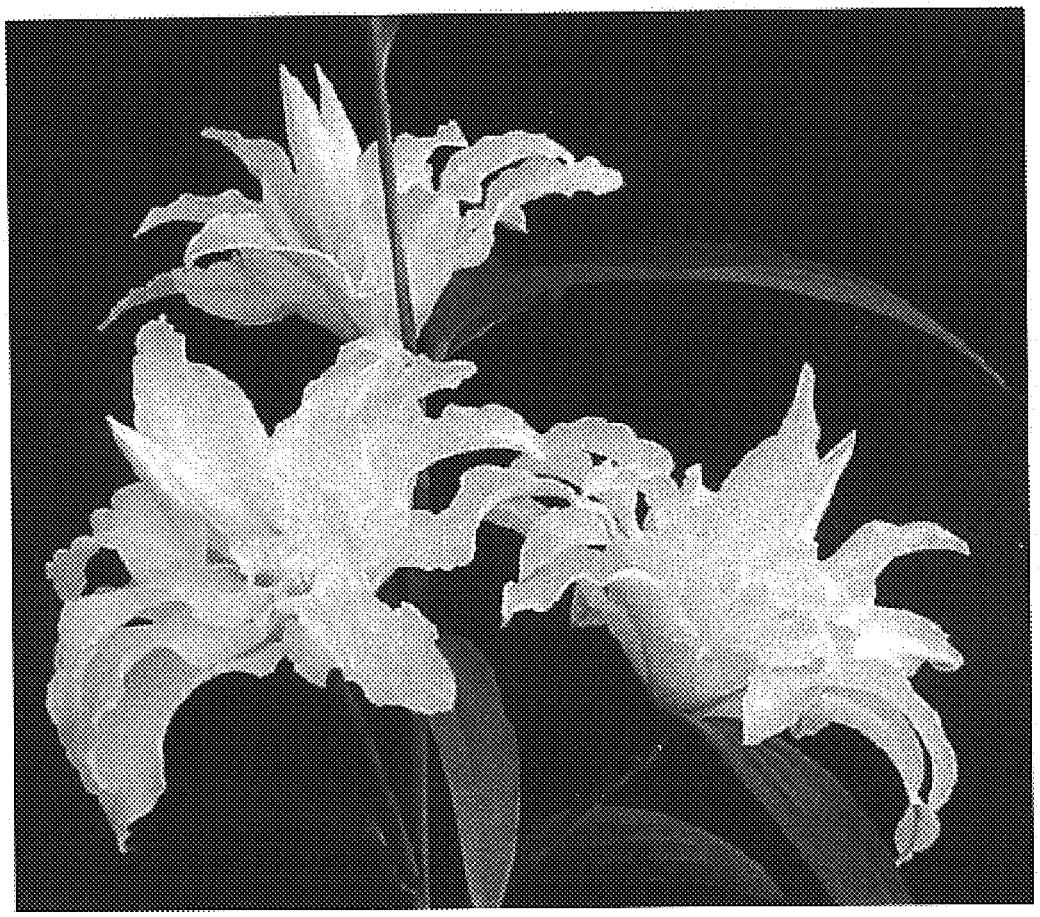

* * * * *